US00PP34614P2

(12) United States Plant Patent
Sidhu

(10) Patent No.: US PP34,614 P2
(45) Date of Patent: Sep. 27, 2022

(54) ***NANDINA* PLANT NAMED 'NANSID1 1'**

(50) Latin Name: *Nandina domestica*
Varietal Denomination: Nansid1 1

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 17/703,392

(22) Filed: Mar. 24, 2022

(30) Foreign Application Priority Data

Apr. 15, 2021 (CA) ..... 21-10461

(51) Int. Cl.
*A01H 5/12* (2018.01)
*A01H 6/72* (2018.01)

(52) U.S. Cl.
USPC ..... Plt./235
CPC ..... *A01H 6/72* (2018.05)

(58) Field of Classification Search
USPC ..... Plt./235
CPC ..... A01H 6/72; A01H 5/12
See application file for complete search history.

*Primary Examiner* — Keith O. Robinson

(74) *Attorney, Agent, or Firm* — Penny J. Aguirre

(57) ABSTRACT

A new cultivar of *Nandina domestica* named 'Nansid11' that is characterized by its new growth that is yellow in color and its dwarf, compact and densely branched plant habit.

2 Drawing Sheets

Botanical classification: *Nandina domestica.*
Variety denomination: 'Nansid11'.

CROSS REFERENCE TO A RELATED APPLICATION

This application claims priority to a Canadian Plant Breeder's Rights Application No. 21-10460 filed on Apr. 15, 2021, under 35 U.S.C. 119(f), the entire contents of which is incorporated by reference herein.

BACKGROUND OF THE INVENTION

The present invention relates to a new and distinct cultivar of *Nandina domestica* and will be referred to hereafter by its cultivar name, 'Nansid11'. 'Nansid11' is a new cultivar of heavenly bamboo shrub grown for use as a landscape plant.

The new cultivar was discovered by the Inventor in spring of 2016 as a naturally occurring branch mutation of *Nandina domestica* 'Gulf Stream' (U.S. Plant Pat. No. 5,656) that was growing in a container at his nursery in Mission, British Columbia, Canada.

Asexual propagation of the new cultivar was first accomplished under the direction of the inventor by tissue culture of meristematic tissue in spring of 2017 in Mission, British Columbia, Canada. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Nansid11' as a unique cultivar of *Nandina.*

1. 'Nansid11' exhibits new growth that is yellow in color.

2. 'Nansid11' exhibits a dwarf, compact and densely branched plant habit.

'Gulf Stream', the parent plant of 'Nansid11', is similar to 'Nansid11' in growth rate and plant habit. 'Gulf Stream' differs from 'Nansid11' in having foliage with new growth that is more green in color. 'Nansid11' can be most closely compared to the cultivar 'NanSid6' (U.S. Plant Pat. No. 29,798). 'NanSid6' is similar to 'Nansid11' in growth rate and plant habit. 'NanSid6' differs from 'Nansid11' in having foliage with new growth that is red in color and in having finer (less wide) foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website listings by Briggs Nursery, BC landscape Nursery Association, Sidhu & Sons Nursery, and Plantsomething BC.

BRIEF DESCRIPTION OF THE DRAWINGS

The accompanying color photographs illustrate the overall appearance and distinct characteristics of two year-old plants as grown outdoors in 1-gallon containers in St. Thomas, Ontario, Canada.

The photograph in FIG. 1 illustrates the overall plant habit and foliage coloration of 'Nansid11'.

Figure 1:
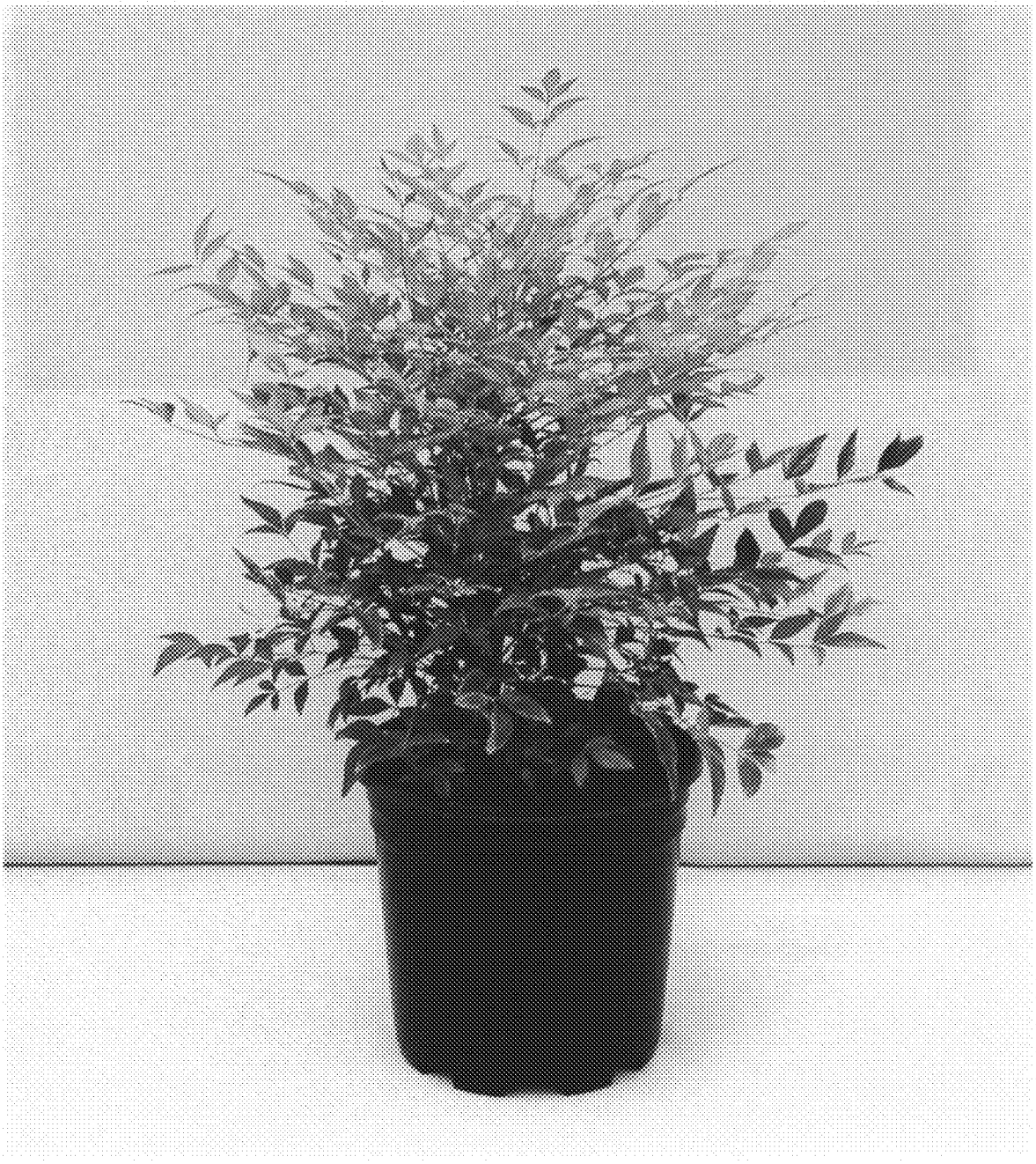
Figure 2:
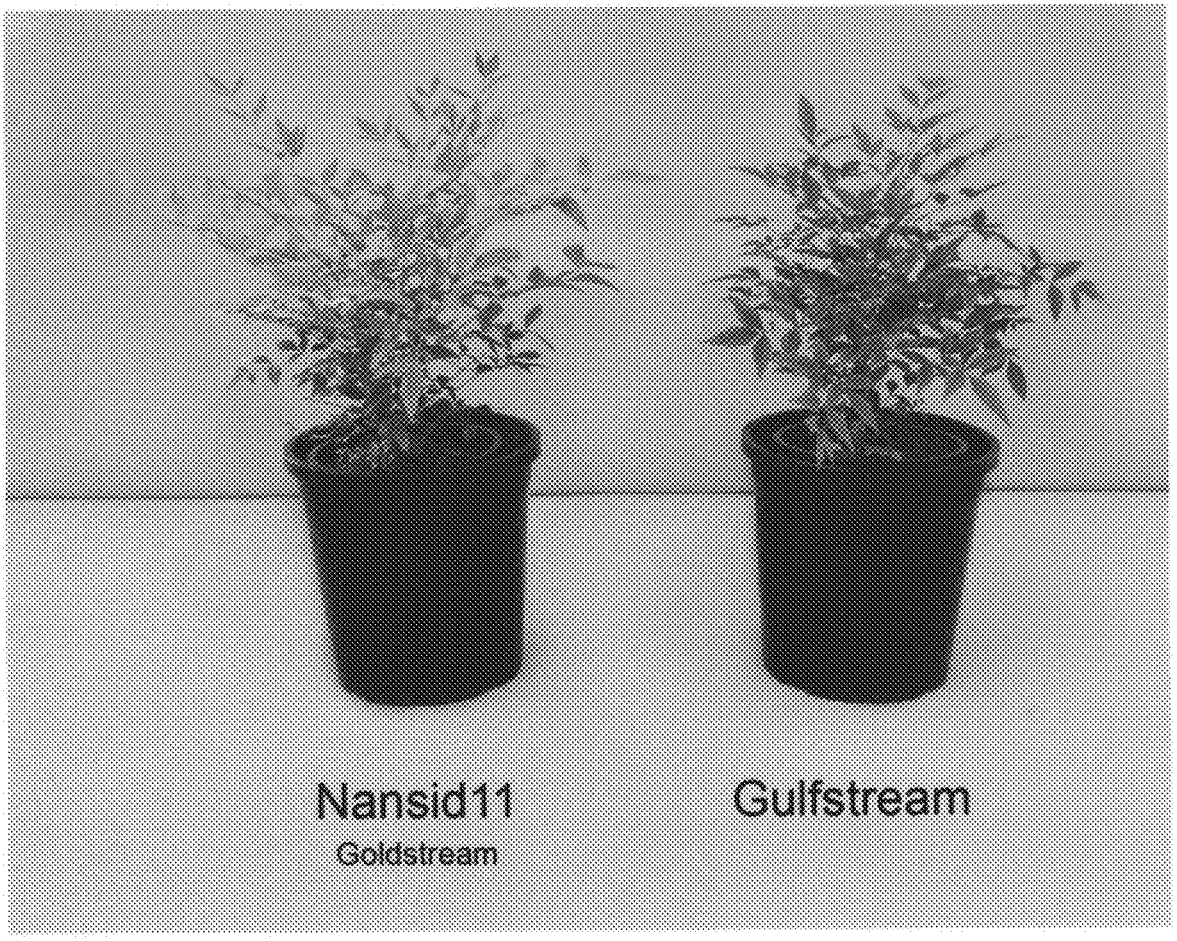

The photograph in FIG. 2 provides a comparison of new growth coloration between 'Nansid11' (left) and 'Gulf Stream' (right).

The colors in the photographs are as close as possible with the digital photography techniques utilized and the color values cited in the detailed botanical description accurately describe the colors of the new *Nandina*.

DETAILED BOTANICAL DESCRIPTION

The following is a detailed description of a 2 year-old plants of the new cultivar as grown outdoors in 1-gallon containers in St. Thomas, Ontario, Canada. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Plant type*.—Evergreen to semi-evergreen shrub.

*Plant habit*.—Upright mounding habit, dwarf, and compact with dense foliage.

*Height and spread*.—Reaches about 39 cm in height and 49 cm in width as a 2 year-old plant in a one-gallon container and abut 75 m in height and width in the landscape.

*Cold hardiness*.—At least in U.S.D.A. Zone 6a.

*Diseases and pests*.—No susceptibility or resistance to diseases or pests has been observed.

*Root description*.—Fibrous, outward spreading by underground rhizomes has not been observed.

*Propagation*.—Tissue culture.

*Root development*.—6 weeks to produce a rooted liner from tissue culture and about 2 growing seasons to produce a finished plant in a one-gallon container.

*Growth rate*.—Moderate.

Stem (cane) description:

*Stem shape*.—Rounded, comprised of clasping petioles.

*Stem strength*.—Strong.

*Stem color*.—Basal woody stem; closest to N200A with 199B fissures, new shoots; 35C, 31C blended with 161A.

*Stem size*.—Mature woody stem; average of 7.5 cm in length and 11.3 mm in width, new shoot; average of 11.5 cm in length and 5 mm in width.

*Stem surface*.—Mature wood; fissured and slightly textured, new shoot; smooth.

*Stem aspect*.—Upright.

*Internode length*.—1.3 cm.

*Branching*.—About 5 new shoots from woody base.

Foliage description:

*Leaf shape*.—Rhomboidal.

*Leaf division*.—Tri-pinnate and bi-pinnate, leaflets occur in opposite pairs, with an average of 33 leaflets per leaf.

*Leaf arrangement*.—Helically alternate.

*Leaf attachment*.—Petiolate.

*Leaflet type*.—Both single foliate and trifoliate leaflets.

*Leaflet base*.—Attenuate.

*Leaflet apex*.—Acuminate.

*Leaflet fragrance*.—None.

*Leaflet venation*.—Pinnate, not conspicuous, matches leaflet color on upper surface, mid rib is slightly protruding on lower surface.

*Leaflet margins*.—Entire.

*Leaflet surface*.—Glabrous on upper and lower surface.

*Leaflet attachment*.—Petiolate and sessile.

*Leaf size*.—Average of 30.4 cm in length and 19.9 cm in width.

*Leaflet size*.—Average of 5.9 cm in length and 2.1 cm in width.

*Leaflet shape*.—Elliptic and lanceolate.

*Leaflet color*.—New growth in spring; 166B to 166D on upper surface and 177D on lower surface, as leaf expands the color gradually changes to more green than 151D with 181D at the margins on upper surface and more yellow than N148D with 181D margins on lower surface; mature leaves 138A on upper surface and 138B on lower surface, fall and winter; leaves 48A to 48B on upper surface 51B lower surface and leaves 11C to 11D on both surfaces.

*Petioles*.—Average of 4.9 cm in length and 2.3 mm in diameter, surface is glabrous and dull, sheath-like clasping base 1.2 cm in length and 1 cm in width, color; new growth in spring; 145B heavily streaked with 70C, summer; 138A, fall to winter; some leaves 50A on both surfaces.

*Petiolules*.—Primary lateral; average of 3.7 cm in length and 1.7 mm in width, surface is glabrous and dull, secondary lateral; average of 1.2 cm in length and 0.7 mm in width, surface is glabrous and dull, similar coloration as petioles.

Inflorescence description: No flowers have been observed on any plants available for data collection and it is presumed to bloom very rarely if it does.

It is claimed:

1. A new and distinct cultivar of *Nandina* plant named 'Nansid11' as herein illustrated and described.

* * * * *